United States Patent [19]

Furuie

[11] Patent Number: 5,431,048

[45] Date of Patent: Jul. 11, 1995

[54] ANALYZER HAVING COVER WITH AN OPERATING AND DISPLAY UNIT

[75] Inventor: Dai Furuie, Kakogawashi, Japan

[73] Assignee: Toa Medical Electronics Co., Ltd., Kobe, Japan

[21] Appl. No.: 963,556

[22] Filed: Oct. 20, 1992

[30] Foreign Application Priority Data

Oct. 22, 1991 [JP] Japan ............... 3-094478 U

[51] Int. Cl.6 .................................. G01D 11/24
[52] U.S. Cl. .................... 73/431; 248/923; 364/708.1
[58] Field of Search .............. 73/431; 108/6, 7, 8, 108/9; 248/921, 922, 923; 364/708.1; 312/298

[56] References Cited

U.S. PATENT DOCUMENTS

| 2,966,257 | 12/1960 | Littlejohn | 73/431 |
| 4,423,631 | 1/1984 | Dold | 73/431 |
| 4,725,106 | 2/1988 | Shields et al. | 312/208 |
| 4,852,032 | 7/1989 | Matsuda et al. | 364/708 |
| 5,107,402 | 4/1992 | Malgouires | 248/921 |
| 5,175,672 | 12/1992 | Conner et al. | 361/393 |

FOREIGN PATENT DOCUMENTS

| 217941 | 10/1958 | Australia | 108/7 |
| 231637 | 1/1986 | Germany | 73/431 |

Primary Examiner—Hezron E. Williams
Assistant Examiner—Daniel S. Larkin
Attorney, Agent, or Firm—Jones, Tullar & Cooper

[57] ABSTRACT

An apparatus for aspirating and analyzing blood, urine or other specimens, in which an operating and display unit is built in the front cover. The operating and display unit is furnished with operation keys and a display screen is rotatably pivoted, at its one end, on the front cover by a the shaft. In this construction, in an automatic analyzer of blood, urine or the like having the operating and display unit built in the front cover, even with the front cover opened, the operation keys may be manipulated and the display screen may be observed easily.

3 Claims, 5 Drawing Sheets

ANALYZER HAVING COVER WITH AN OPERATING AND DISPLAY UNIT

BACKGROUND OF THE INVENTION

The present invention relates to an apparatus for aspirating and analyzing a specimen, such as blood, urine or the like, and more particularly to an analyzer having an opening cover which is enhanced in its controllability and ease of reading of a display screen. The apparatus includes an analyzer having an operating unit or a display unit attached to the opening cover.

In an apparatus for aspirating and analyzing specimens such as blood, a structure provided with an opening cover has been hitherto known. FIG. 1 is a partially cut-away side view of such a conventional apparatus. Numeral 10 denotes the main body of an automatic analyzer, and 12 is a front cover. The front cover 12 can be opened and closed in the direction of arrow A. The double dot chain line indicates the opened state of the front cover 12. Usually, the apparatus is used in the state where the front cover 12 is lowered, that is, with the front cover 12 in the closed states. Numeral 26 denotes an opening in the front cover 12.

When adjusting the sensitivity, or in the event of maintenance or the like, the front cover 12 is opened, and the work is done, that is, the units built in the main body of the apparatus are adjusted, and the control knobs (volume control knob etc.) of the printed board (electric circuit) as regulated.

Numeral 20 denotes an operating and display unit for displaying measured results and for setting various conditions. The unit 20 is provided inside of the front cover 12, and is designed so that operation keys 24 can be touched, and a display screen 22 read (observed) from outside.

In such an adjustment procedure or the like, while actually measuring, it is sometimes necessary to perform an operation by observing a measured result shown on the display screen 22. Furthermore, on the basis of the display result, the data must be entered from the operation keys 24.

In the conventional apparatus, with the front cover 12 opened, it was not possible to enter the data through the operation keys 24 or read (observe) the display screen 22 from the front side. Accordingly, on every occasion where adjustment or maintenance was required, the front cover had to be opened and closed, which was very troublesome.

OBJECT AND SUMMARY OF THE INVENTION

It is therefore a primary object of the present invention to provide an analyzer having an operating unit or display unit built in the front cover, and capable of easily manipulating or observing the display screen with the cover opened.

To achieve the above object, the present invention provides an analyzer having a cover with an operating and display unit built in the front cover, wherein the operating and display unit is rotatably pivoted by a shaft so that operation keys may be manipulated and the display screen may be observed, with the cover opened.

The present invention also provides an analyzer having a cover, with an operating and display unit built inside of the front cover rotatably fitted to the apparatus main body, so that operation keys of the operating and display unit may be touched and the display screen may be observed, through an opening in the front cover, wherein the operating and display unit is rotatably pivoted on the front cover by a shaft at the end part of the operating and display unit.

By rotating the operating and display unit with the front cover opened, the operating and display unit is directed forward, so that the operating unit may be touched and the display screen may be observed, easily from the front side. Usually, the front cover is lowered and closed.

DETAILED DESCRIPTION OF THE PREFERRED EMBODIMENTS

Figure 1:
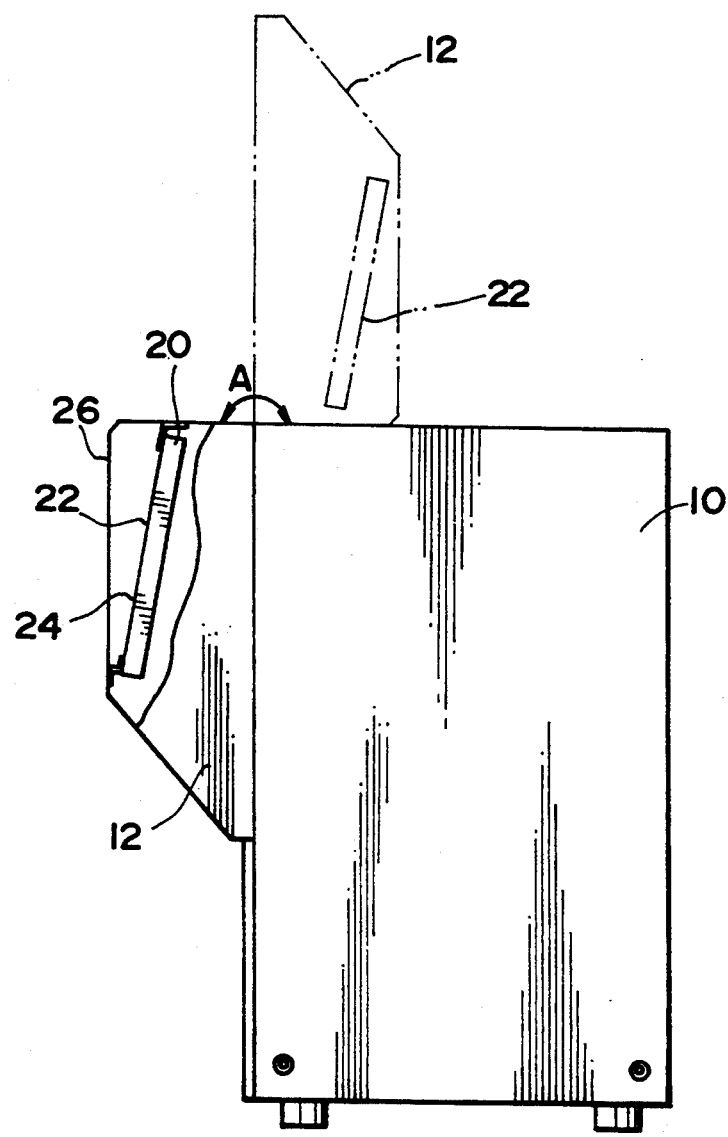
FIG. 1 is a side view showing an example of a conventional analyzer having a cover.

Referring now to FIGS. 2-5, some of the preferred embodiments of the present invention are described in detail below.

The analyzer having a cover of the present invention comprises, as shown in FIG. 2 to FIG. 5, an operating and display unit 20 built in a front cover 12, wherein the operating and display unit 20 is rotatably pivoted by a shaft 28 so that the operation keys 24 may be manipulated and the display screen 22 may be observed, with the cover 12 opened.

The analyzer having the cover of the present invention also comprises, as shown in FIG. 2 to FIG. 5, an operating and display unit 20 built inside of the front cover 12 rotatably fitted to the apparatus main body 10, so that the operation keys 24 of the operating and display unit 20 may be touched and the display screen 22 may be observed, through an opening 26 in the front cover 12, wherein the operating and display unit 20 is rotatably pivoted on the front cover 12 by a shaft 28 at the end part of the operating and display unit 20.

Figure 2:
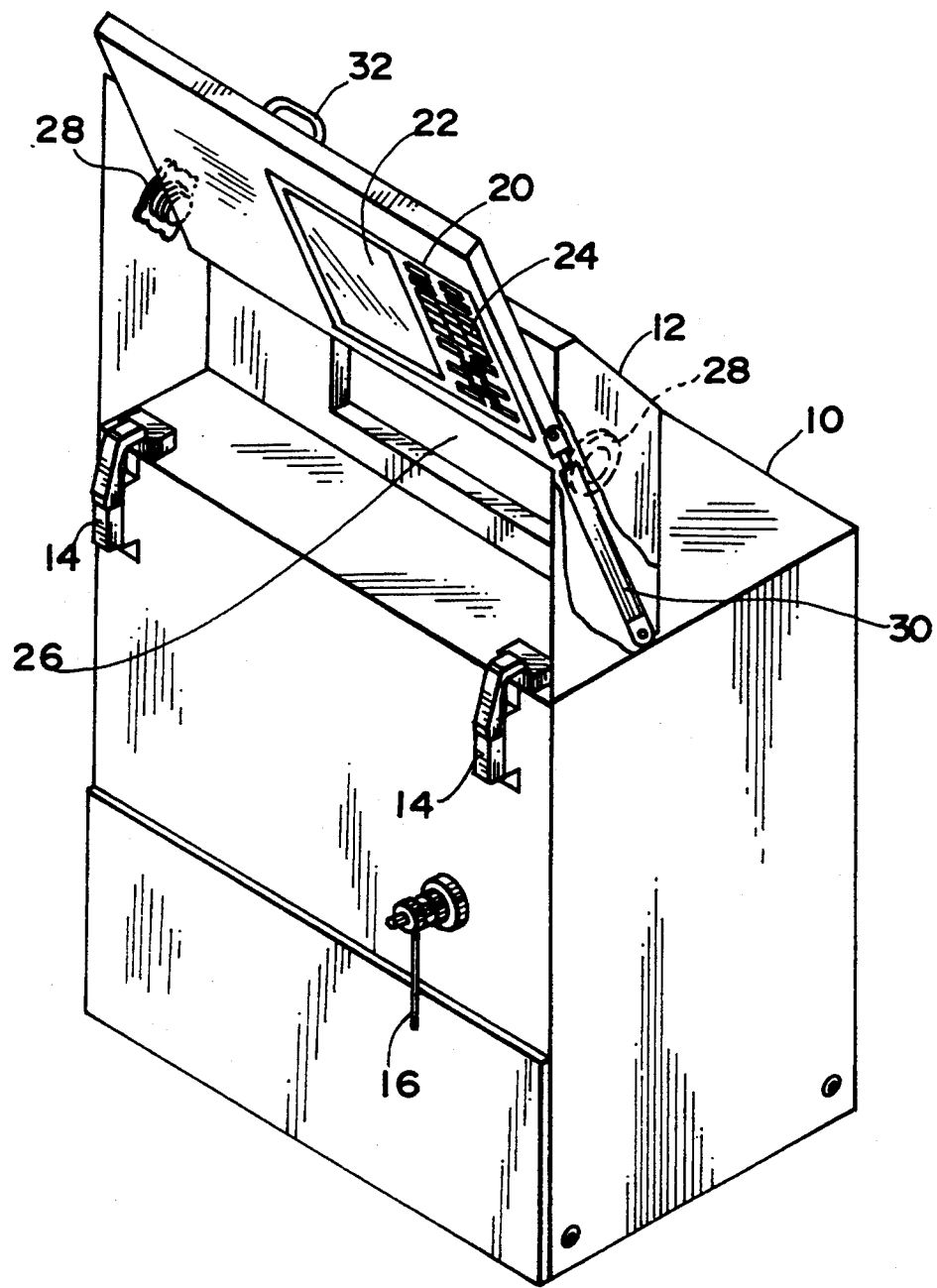
FIG. 2 is a partially cut-away perspective view showing an embodiment of an analyzer having cover according to the present invention.
Figure 3:
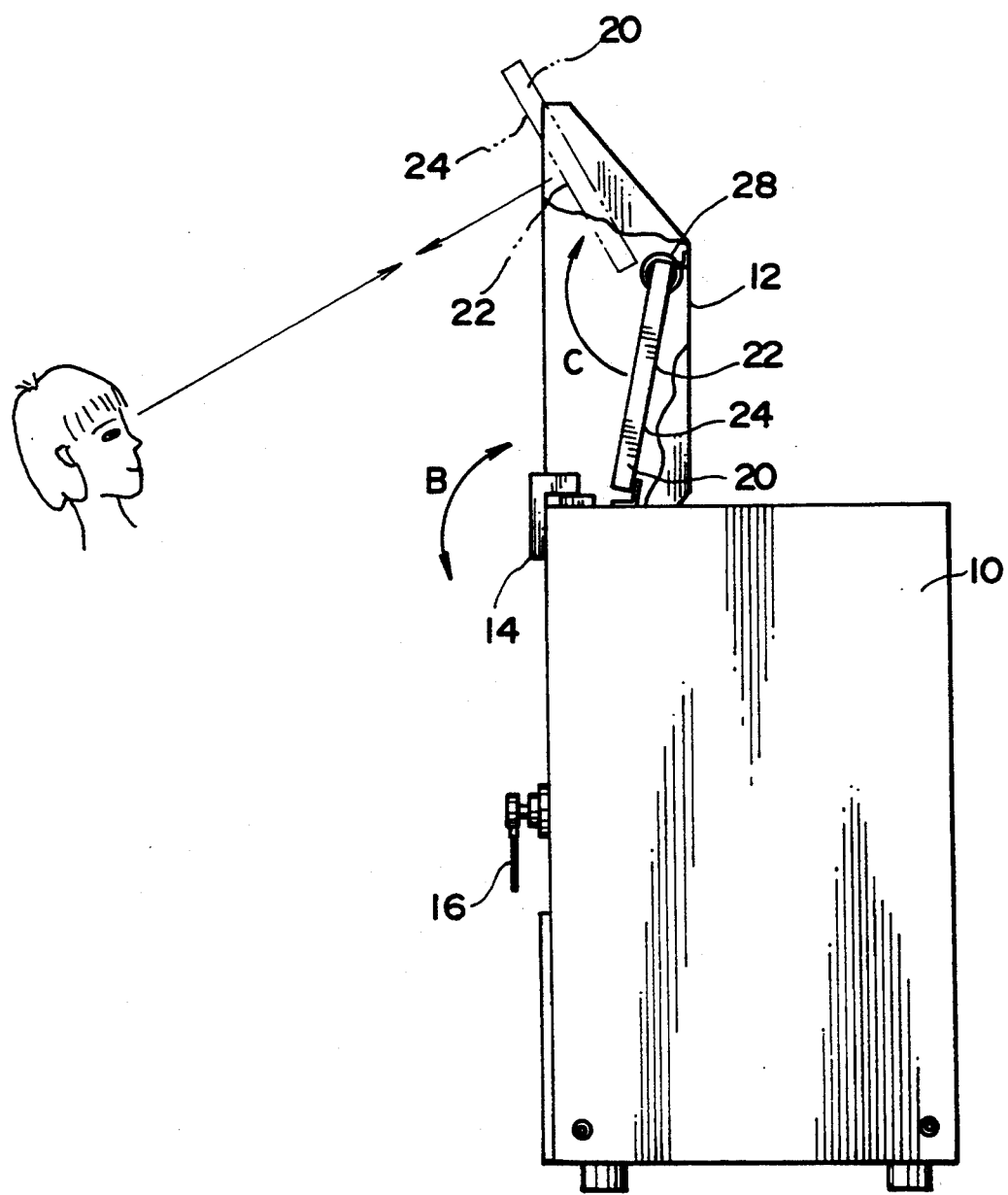
FIG. 3 is a partially cut-away side view of the apparatus shown in FIG. 2, showing the front cover in the opened state.
Figure 4:
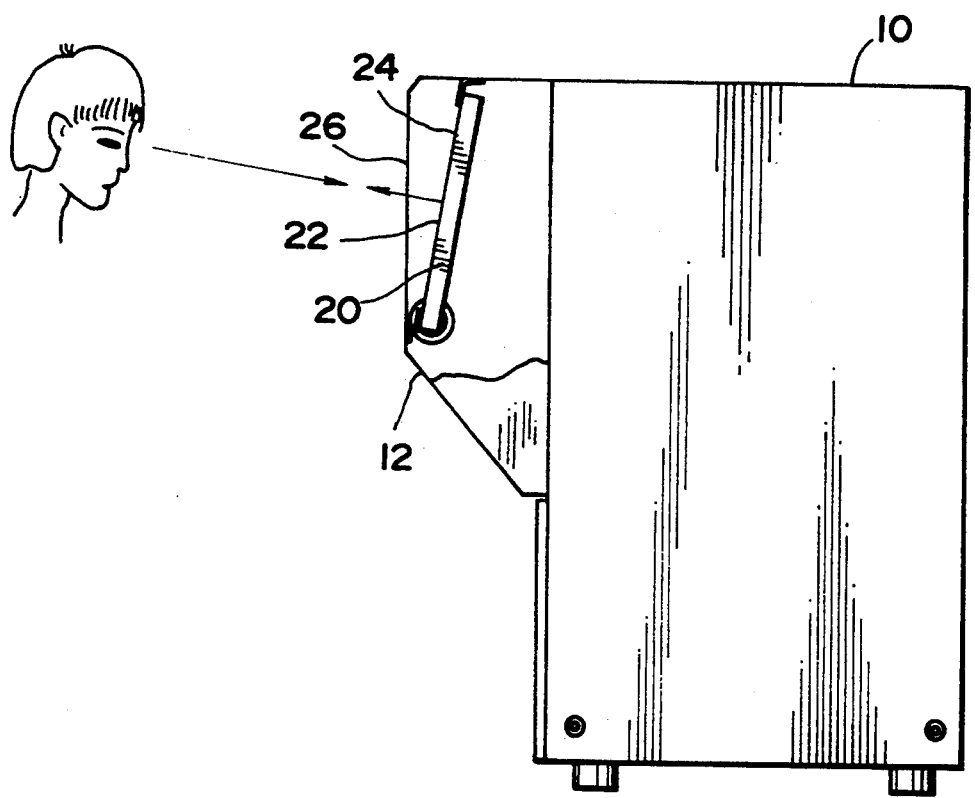
FIG. 4 is a partially cut-away side view of the apparatus shown in FIG. 2, showing the front cover in the closed state.

As shown in FIG. 2 and FIG. 3, by rotating the operating and display unit 20 with the front cover 12 opened, the operating part and the display screen are directed forward, so that the operating part may be touched and the display screen may be observed easily from the front side. Usually, as shown in FIG. 4, the front cover 12 is lowered and closed.

FIG. 2 is a partially cut-away perspective view (cut out around a gas spring 30) showing an embodiment of the present invention, and FIG. 3 is its partially cut-away side view (cutting out a part of the front cover), showing the opened state of the front cover 12.

In this embodiment, for example, an automatic blood analyzer is explained. Numeral 10 is then main body of the automatic blood analyzer, and 12 is the front cover that can be opened and closed. Numeral 14 is a mounting bracket, which couples together the main body 10 and front cover 12, and rotates the front cover 12 up and down in the direction of arrow B to open or close it. FIG. 4 shows the closed state of the front cover by rotating downward.

On the front side of the main body 10, as aspiration tube 16 for aspirating the specimen is provided. Numeral 20 is the operating and display unit, comprising operation keys 24 for entering setting data, and display screen 22 for displaying measurement results and other information. This operating and display unit 20 is rotatably built inside of the front cover 12. An opening 26 is formed in the front surface of the front cover 12, so that the operation keys 24 may be touched and adjusted, and the display screen 22 may be observed, from outside of the apparatus. Besides, as shown in FIG. 3, with the operating and display unit lowered by opening the front cover, the top surface of the operating and display unit 20 is rotatably pivoted on the front cover 12 by a shaft 28 of a TOK Bearing (trade name) or the like. At a slightly lower side of the support part of the shaft 28, one end of a shock absorber, such as a gas spring 30, is rotatably fitted. The other end of the gas spring 30 is fitted to the front cover 12. Numeral 32 is a handle of the operating and display unit 20 (FIG. 2).

Figure 5:
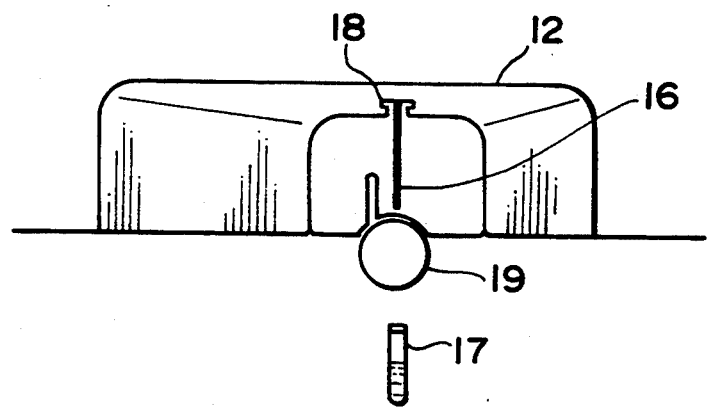
FIG. 5 is a front view around a specimen aspiration tube of the front cover.

FIG. 5 is a front view around the specimen aspiration tube 16 of the front cover 12. Numeral 18 is a notch, which allows the aspiration tube 16 to extend out of the cover 12 from beneath even in the closed state of the front cover 12. Numeral 17 is a specimen container filled with blood sample, and 19 is a container (spit, waste cup) for cleaning the specimen aspiration tube 16.

Usually, as shown in FIG. 4, the front cover 12 is lowered, and the apparatus is used in the cover closed state. At this time, the operation keys 24 and display screen 22 of the operating and display unit 20 are directed forward (the leftward direction in FIG. 4), and therefore the operation keys 24 may be touched and the display screen 22 may be observed from outside the apparatus through the opening 26.

In the manipulation for sensitivity adjustment or the like, as shown in FIG. 3, the front cover 12 is rotated and lifted, and the units built in the main body of the apparatus and the volume control knob of the printed substrate (board) are adjusted from the front side of the apparatus. With the front cover 12 opened, the operation keys 24 and display screen 22 are directed backward (in the rightward direction in FIG. 3), and are turned upside down.

Accordingly, as indicated by the double dot chain line, by rotating the operating and display unit 20 in the direction of arrow C around the shaft 28, the vertical direction of the operation keys 24 and display panel 22 is inverted, and the operation keys 24 and display screen 22 are directed forward, obliquely in the downward direction, so that it is easy to manipulate and easy to observe for the operator standing in front of the apparatus. Usually, the operating and display unit 20 is fixed to the front cover 12. The fixing means (not shown) may be a known one. If it is necessary to rotate the operating and display unit 20, its fixing may be released, and the operating and display unit 20 may be rotated by holding a grip 32.

In the present invention, as the means for supporting the other end of the operating and display unit 20, it is preferable to use the gas spring 30 as mentioned above. Or the gas spring 30 may be replaced by any substitute so long as the force acts in the extending direction. Initially, the gas spring 30 is slightly elongated. To rotate the operating and display unit 20, the gas spring 30 must be contracted, and force is required, but when rotated to a certain extent, to the contrary, the gas spring 30 is elongated, and by this elongating force, and operating and display unit 20 may be rotated very lightly. Or it rotates spontaneously (automatically). It consequently stops when rotating to the full. In this state, it is possible to temporarily fix by the fixing means (not shown).

As the shaft 28, it is desired to use one having a load in the rotating direction. This is because the rotary motion of the operating and display unit 20 becomes slower and smoother. Such rotary shaft is available from the TOK Bearing Co. under the trade name of TOK Bearing.

When opening and closing the front cover 12 up and down, it is preferred to install the shaft 28 in the lower pat of the operating and display unit 20. This is because, as mentioned above, the operation keys 24 and display screen 22 are directed forward, obliquely in the downward direction. But it may be installed in the upper part of the operating and display unit 20. In such a case, however, the operation keys 24 and display screen 22 are directed forward, obliquely in the upward direction.

So far the case of rotating the front cover 12 vertically has been explained. But the cover 12 may be opened and closed laterally. By the same reason as mentioned above, when opening the cover 12 to the left side, it is desired to install the shaft at the right side of the operating and display unit, and when opening the cover 12 to the right side, it is preferably to install it at the left side.

The analyzer having the cover of the present invention is thus constructed, and it is possible to manipulate the operation keys and observe the display screen while performing adjustments and servicing with the front cover opened, which brings about the effect of enhancing working efficiency.

Having described preferred embodiments or the present invention with reference to the accompanying drawings, it is to be understood that the present invention is not limited to those precise embodiments, and that various changes and modifications may be effected therein by one skilled in the art without departing from the scope or spirit of the present invention as defined in the appended claims.

What is claimed is:

1. In an analyzer of an apparatus for aspirating and analyzing specimens, the improvement comprising:
   a front cover;
   means for rotatably mounting said front cover to the apparatus to assume open and closed states;
   an operating and display unit including operating keys and a display screen; and
   means for rotatably mounting said operating and display unit to said front cover so that the operating keys may be manipulated and the display screen observed when said front cover is in its open state or closed state, wherein said means for rotatably mounting said front cover to the apparatus and said means for rotatably mounting said operating and display unit to said front cover each define a rotatable movement axis, and wherein the direction of the rotatable movement axis of said front cover and the direction of the rotatable movement axis of said operating and display unit are substantially parallel.

2. The improvement as defined in claim 1, wherein the means for rotatably mounting said operating and display unit includes a shaft located at one end of said operating and display unit.

3. The improvement as defined in claim 1, wherein said front cover has an opening so that the operating keys may be manipulated and the display screen observed when said front cover is in its closed state, and wherein said operating and display unit is pivoted by said means for rotatably mounting said operating and display unit to said front cover so that the operating keys may be manipulated and the display screen observed when said front cover is in its opened state.

* * * * *